(12) United States Patent
Piercey et al.

(10) Patent No.: US 10,742,048 B2
(45) Date of Patent: Aug. 11, 2020

(54) WEARABLE ELECTRONIC DEVICE WITH A CASEBACK HAVING MULTIPLE, ARC-SHAPED, FERROUS, METAL CONTACTS

(71) Applicant: Fossil Group, Inc., Richardson, TX (US)

(72) Inventors: Brad William Piercey, Oak Point, TX (US); Ryan Griffin Geraghty, San Francisco, CA (US); Sean E. Daley, San Jose, CA (US); Brad D. Brinson, San Francisco, CA (US); Alexander J. Brown, Foster City, CA (US); Timothy Simeon Golnik, Dallas, TX (US)

(73) Assignee: Fossil Group, Inc., Richardson, TX (US)

( * ) Notice: Subject to any disclaimer, the term of this patent is extended or adjusted under 35 U.S.C. 154(b) by 0 days.

(21) Appl. No.: 16/053,545

(22) Filed: Aug. 2, 2018

(65) Prior Publication Data
US 2020/0044466 A1 Feb. 6, 2020

(51) Int. Cl.
*H01M 10/44* (2006.01)
*H01M 10/46* (2006.01)
(Continued)

(52) U.S. Cl.
CPC ........ *H02J 7/0042* (2013.01); *A61B 5/02438* (2013.01); *A61B 5/681* (2013.01);
(Continued)

(58) Field of Classification Search
CPC .......... H02J 7/355; H02J 7/025; H02J 7/0045; H02J 5/005; H02J 50/90; H02J 50/10
(Continued)

(56) References Cited

U.S. PATENT DOCUMENTS

| 9,557,716 B1 | 1/2017 | Inamdar |
| 2013/0325394 A1 | 12/2013 | Yuen et al. |

(Continued)

OTHER PUBLICATIONS

Macy's, Q Gen 2 Marshal Stainless Steel Bracelet Touchscreen Smart Watch 45 mm FTW2109, Prior to Aug. 2, 2018, 5 pages, http://www.macys.com/shop/product/fossil-q-gen-2-marshal-stainless-steel-bracelet-touchscreen-smart-watch-45mm-ftw2109?ID=2921866, USA.

*Primary Examiner* — Edward Tso
(74) *Attorney, Agent, or Firm* — Rutan & Tucker, LLP

(57) ABSTRACT

A caseback has multiple, arc-shaped, ferrous, metal contacts that serve a dual purpose. The metal contacts i) establish an input connection between a battery for the wearable electronic device and charging prongs of a charger and ii) establish a magnetic coupling between the wearable electronic device and multiple magnets in the charger to hold the metal contacts of the wearable electronic device and the charging prongs of the charger in place during a charging of the battery. A male extension extends from a surface of the caseback to couple into a female receptor of the charger. i) The ferrous metal contacts' relationship with a positioning of the magnetics in the charger in combination with ii) the male extension coupling into the female receptor use magnetic and mechanical coupling to establish and control an alignment of the metal contacts with the charging prongs in three dimensions, a Z-axis, an X-axis, and a Y-axis.

20 Claims, 13 Drawing Sheets

(51) Int. Cl.
*H02J 7/00* (2006.01)
*G06F 1/16* (2006.01)
*A61B 5/024* (2006.01)
*H04B 1/3827* (2015.01)
*G04G 19/06* (2006.01)
*G04G 21/02* (2010.01)
*A61B 5/00* (2006.01)
*G06F 3/0481* (2013.01)

(52) U.S. Cl.
CPC .......... *G04G 19/06* (2013.01); *G04G 21/025* (2013.01); *G06F 1/163* (2013.01); *G06F 1/1635* (2013.01); *G06F 1/1656* (2013.01); *H04B 1/385* (2013.01); *G06F 1/1637* (2013.01); *G06F 3/0481* (2013.01)

(58) Field of Classification Search
USPC ......... 320/107, 108, 114, 115; 968/446, 470
See application file for complete search history.

(56) References Cited

U.S. PATENT DOCUMENTS

| | | |
|---|---|---|
| 2014/0142403 A1 | 5/2014 | Brumback et al. |
| 2015/0305974 A1* | 10/2015 | Ehrenreich .......... A61H 23/004 601/46 |
| 2016/0180999 A1 | 6/2016 | Rattner et al. |
| 2016/0246453 A1 | 8/2016 | Vonshak et al. |
| 2017/0346320 A1 | 11/2017 | Jeong et al. |

* cited by examiner

1100

Metal rings

1150

Metal rings

WEARABLE ELECTRONIC DEVICE WITH A CASEBACK HAVING MULTIPLE, ARC-SHAPED, FERROUS, METAL CONTACTS

FIELD

The design generally relates to wearable electronics devices and the caseback for the wearable electronic device.

BACKGROUND

Traditionally, watches can recharge their battery in two ways. First, rechargeable watches either use physical pins or contact pads to connect from the wristwatch to the charger cable. The physical pins typically lock a coupling between a watch and its charger to connect in a single static position. Traditional charging pins are limiting due to the exact alignment and dexterity needed to join the watch to the charger. Alternatively, a wireless charging method is used to inductively charge a watch using one of several industry standards. Yet, wireless charging requires longer charging periods, which can be too much time for practicality, and generate significant heat to fully charge. While having pins is optimal over wireless for speed, traditionally on other products, the "pinned" embodiment locks you into a very limited set of static positions in which the charger can mate to the watch.

SUMMARY

In general, a wearable electronic device has a housing and a processor in the housing. The processor can process commands to present an onscreen display on a display screen to enable the wearer of the electronic device to select a number of different operations. The wearable electronic device also includes a communication circuit in the housing. The communication circuit can transmit wirelessly to another computing device cooperating with the electronic device. The wearable electronic device has a computer readable storage medium, in the housing, accessible to the processor such that the processor stores instructions executable by the processor to generate different operations on the onscreen display.

A wearable electronic device has a caseback for the backside of the device. The caseback has multiple, arc-shaped, ferrous, metal contacts that serve a dual purpose. The arc-shaped, ferrous, metal contacts i) establish a physical electrical input connection between a battery for the wearable electronic device and charging prongs of an external electrical charger and ii) establish a magnetic coupling between the wearable electronic device and multiple magnets in the external electrical charger to hold the metal contacts of the wearable electronic device and the charging prongs of the external electrical charger in place during a charging of the battery for the wearable electronic device. A male extension extends from a surface of the caseback to couple into a female receptor of the external electrical charger. i) The multiple, arc-shaped, ferrous, metal contacts' relationship with a positioning of the magnetics in the external electrical charger in combination with ii) the male extension of the caseback coupling into the female receptor of the external electrical charger use magnetic and mechanical coupling to establish and control an alignment of the metal contacts with the charging prongs in three dimensions, a Z axis, an X axis, and a Y axis.

These and other designs are discussed.

BRIEF DESCRIPTION OF THE DRAWINGS

The multiple drawings refer to the example embodiments of the design.

Figure 1:
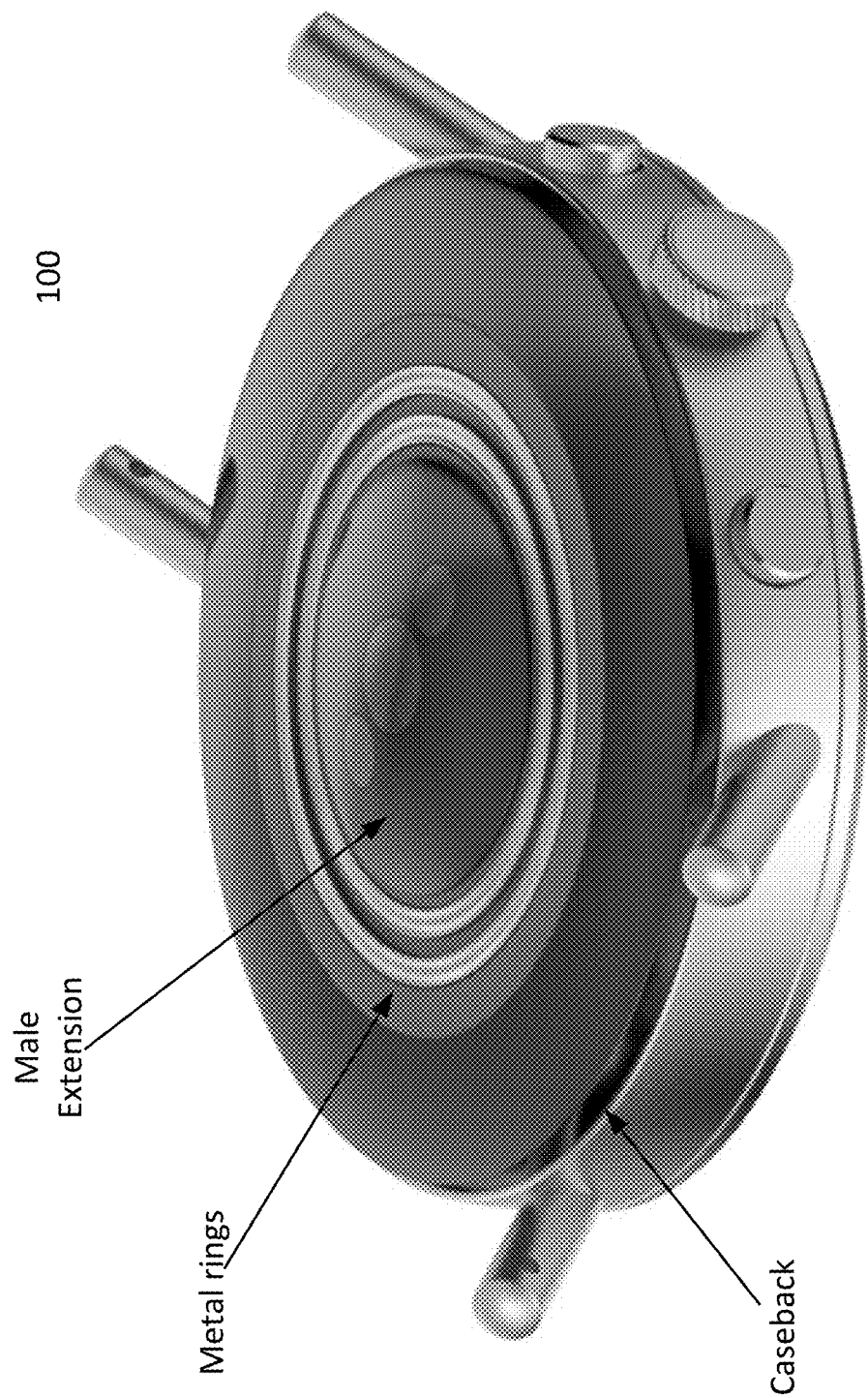
FIG. 1 illustrates an embodiment of a diagram of a caseback having multiple, arc-shaped, ferrous, metal contacts that serve a dual purpose.

While the design is subject to various modifications and alternative forms, specific embodiments thereof have been shown by way of example in the drawings and will herein be described in detail. The design should be understood to not be limited to the particular forms disclosed, but on the contrary, the intention is to cover all modifications, equivalents, and alternatives falling within the spirit and scope of the design.

DETAILED DISCUSSION

In the following description, numerous specific details are set forth, such as examples of wearable electronic devices, named components, connections, number of seals, etc., in order to provide a thorough understanding of the present design. It will be apparent; however, to one skilled in the art that the present design may be practiced without these specific details. In other instances, well known components or methods have not been described in detail but rather in a block diagram in order to avoid unnecessarily obscuring the present design. Thus, the specific details set forth are merely exemplary. The specific details discussed in one embodiment may be reasonably implemented in another embodiment. The specific details may be varied from and still be contemplated to be within the spirit and scope of the present design.

The following drawing and text describe various example implementations of the design.

FIG. 1 illustrates an embodiment of a diagram of a caseback having multiple, arc-shaped, ferrous, metal contacts, such as physical pins, contact pads, terminals, prongs, etc., that serve a dual purpose. The arc-shaped, ferrous, metal contacts i) establish a physical electrical input connection between a battery for the wearable electronic device and charging prongs of an external electrical charger, rather than a wireless electrical coupling, and ii) establish a magnetic coupling between the wearable electronic device and multiple magnets in the external electrical charger to hold the metal contacts of the wearable electronic device and the charging prongs of the external electrical charger in place during a charging of the battery for the wearable electronic device.

The arc-shaped, ferrous, metal contacts may take the form, for example, of either i) two or ii) four concentric metal contact rings on the surface of the caseback. The arc-shaped, ferrous, metal contacts in combination with the magnets located spatially positioned around a center of the external electrical charger are used to magnetically hold the charger prongs of the external electrical charger to the caseback side of the smart watch.

The caseback also has a male extension. The male extension extends from a surface of the caseback. A heart rate sensor may be located in the male extension of the wearable electronic device. The heart rate sensor is electrically connected to the battery. Note, the wearable electronic device may be a smart watch, Activity tracker, etc.

Figure 2:
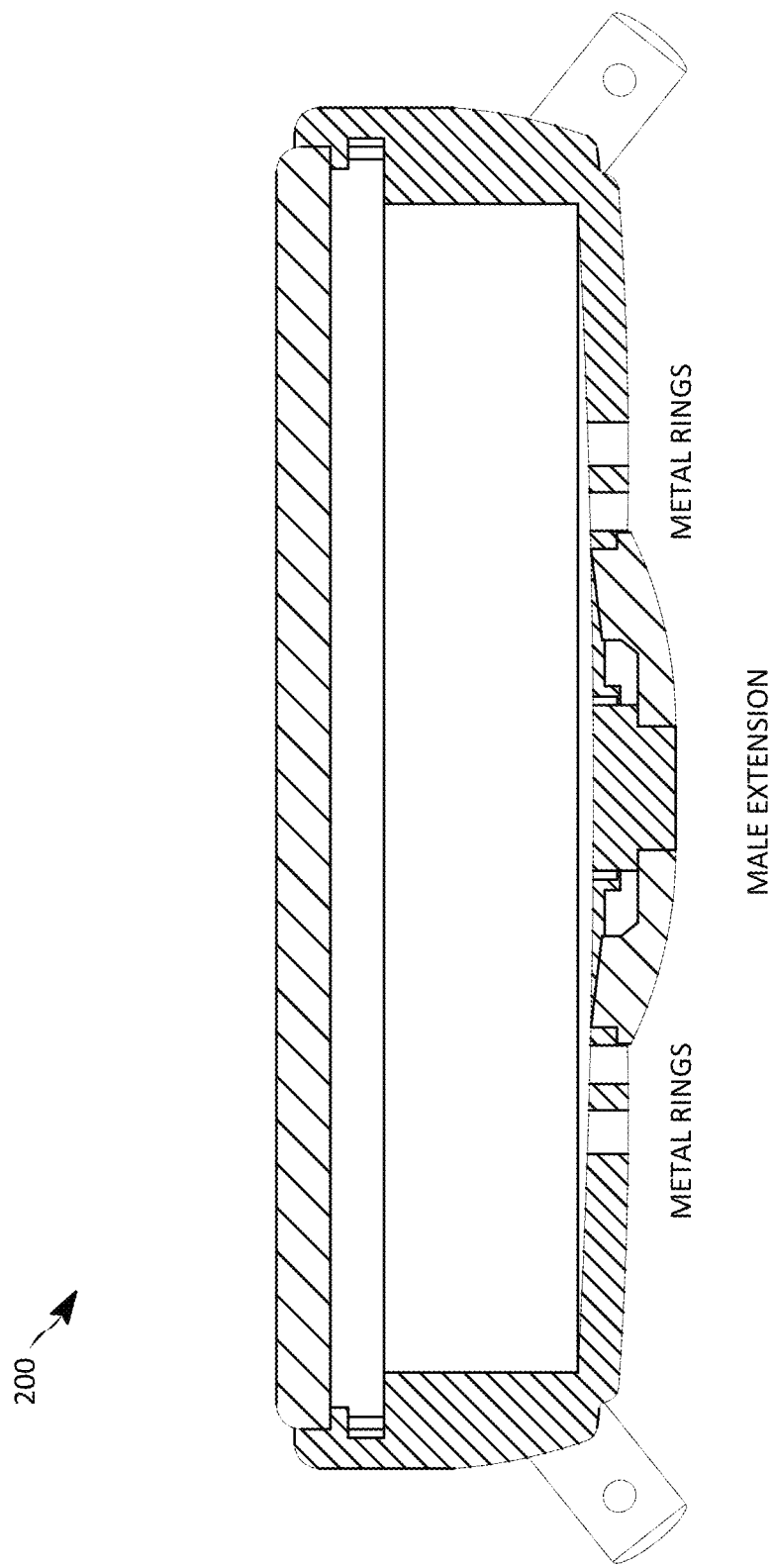
FIG. 2 illustrates a diagram of an embodiment of a caseback having a male extension extending from a surface of the caseback to couple into a female receptor of the external electrical charger.
Figure 3:
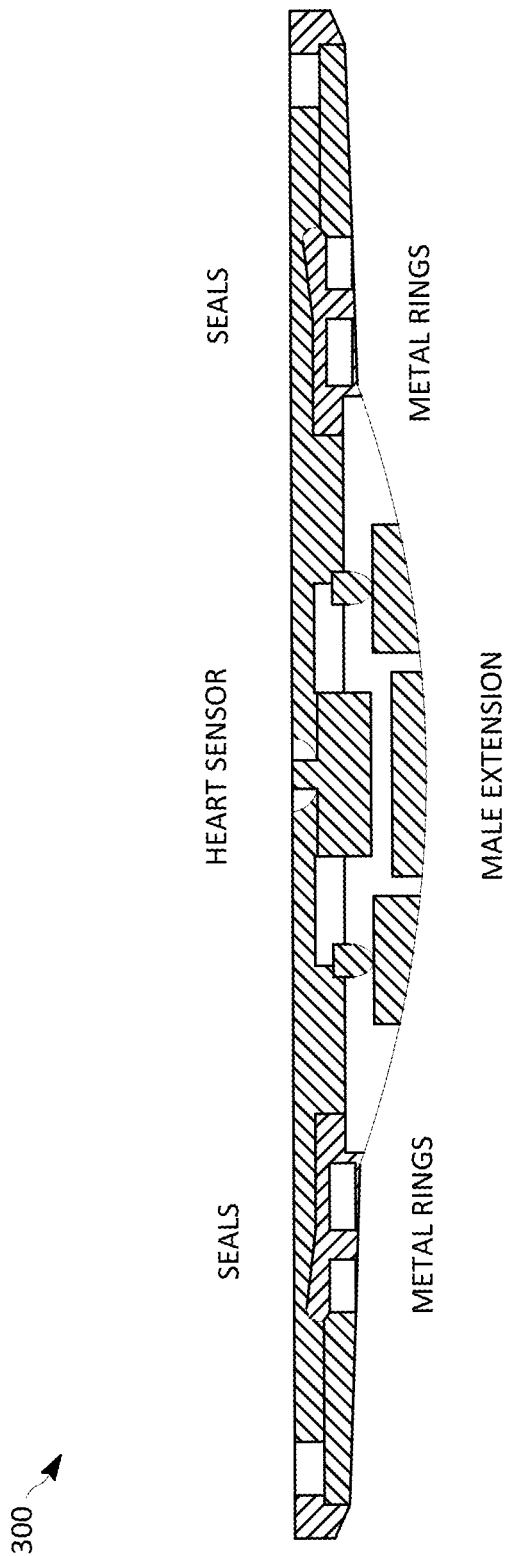
FIG. 3 illustrates a diagram of an embodiment of the male extension extending from the surface of the caseback that houses the heart rate sensor and is surrounded by the concentric metal contact rings.

FIG. 2 illustrates a diagram of an embodiment of a caseback having a male extension extending from a surface of the caseback to couple into a female receptor of the external electrical charger. The male extension may not be a uniform curved surface for the entire length of the back of the wearable electronic device but rather an extension in the Z axis from the rest of the surface of the wearable electronic device. Instead, the male extension can be more of a bump off the surface. (See FIG. 3) FIG. 3 illustrates a diagram of an embodiment of the male extension extending from the surface of the caseback that houses the heart rate sensor and is surrounded by the concentric metal contact rings.

Referring back to FIG. 2, in an embodiment, the male extension creates a mechanical 'male-female' seating with a matching shaped female receptor in the external electrical charger, where the male extension takes the form and shape of a curved dome rising in the Z direction from the surface plane of the caseback. This curved dome spans merely a portion of the surface plane of the caseback and does not extend for an entire length of the caseback. In an embodiment, the curved dome may span the surface plane of the caseback. Other than the metal contacts, the base material of the caseback can be made of i) ceramic, ii) plastic, or iii) a combination of both.

The "bump" or extension for the optical heart rate tracking creates a mechanical 'male-female' seating or "self seat". The bump can be made of i) glass, ii) ceramic, iii) plastic, or iv) a combination of all three. In an embodiment, the bump or extension takes the form and shape of an oval dome rising from the surface plane of the case back. The charger generally has a matching shaped female receptor in the external electrical charger for the different shapes the male extension may be implemented in.

Next, i) the multiple, arc-shaped, ferrous, metal contacts' relationship with a positioning of the magnetics in the external electrical charger in combination with ii) the male extension of the caseback's coupling into the female receptor of the external electrical charger use magnetic and mechanical coupling to establish and control an alignment of the metal contacts with the charging prongs/pins/contacts of the external electrical charger in three dimensions, a Z axis, an X axis, and a Y axis.

The male extension extending from the surface of the caseback can be a mechanical oval dome that houses one or more sensors including the heart rate sensor. The concentric metal contact rings and mechanical oval dome mate to the external electrical charger to combine to provide a user experience with the external electrical charger to achieve a 360 degree rotation between the concentric metal contact rings and the charger prongs via magnetic attraction, mechanical coupling, and automatic centering.

Figure 4:
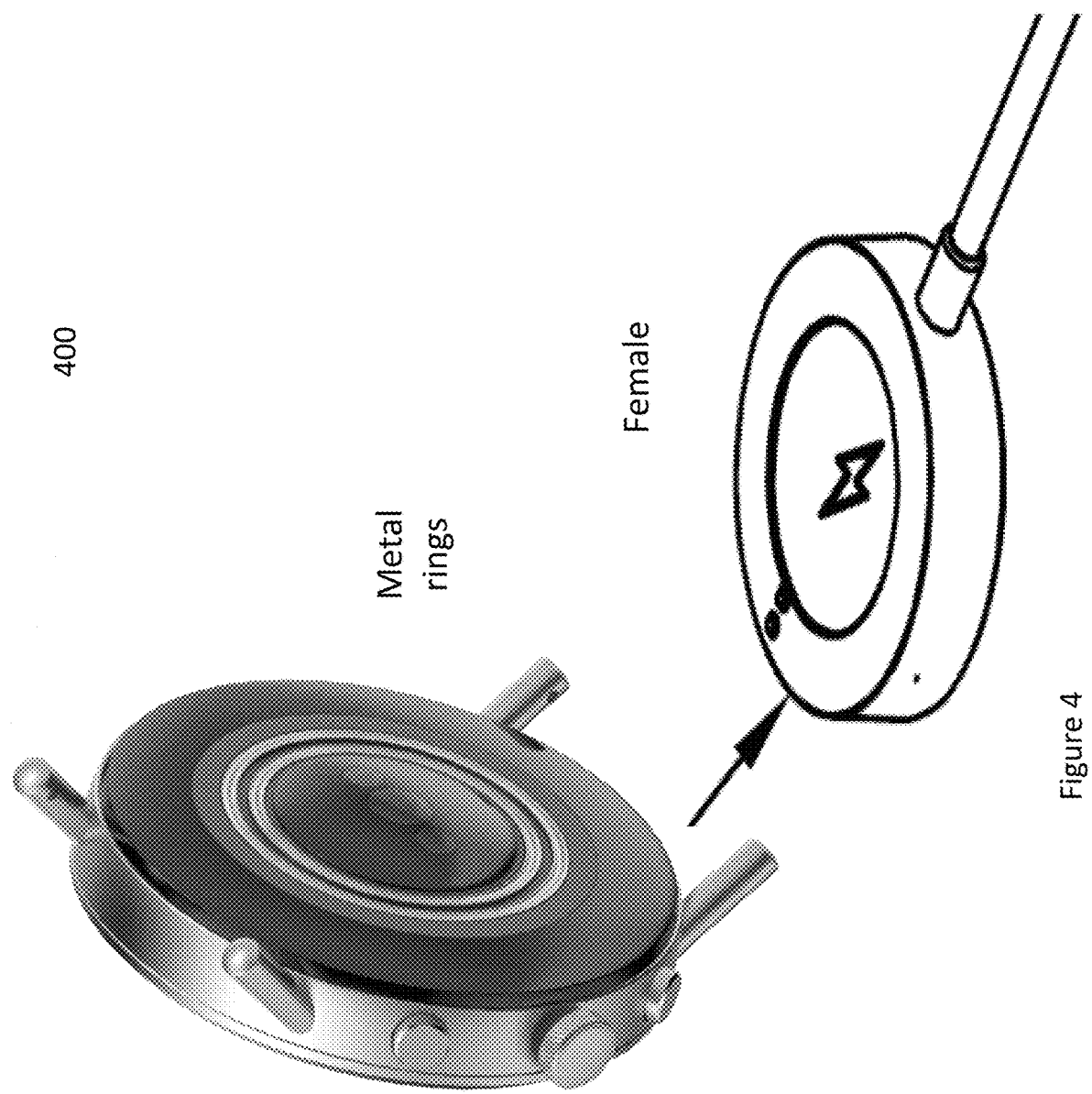
FIG. 4 illustrates an embodiment of the male extension of the caseback, where the male extension has a semi-circular or at least oval shape.

FIG. 4 illustrates an embodiment of the male extension of the caseback, where the male extension has a semi-circular or at least oval shape. A corresponding matching oval depression in the female receptor of the external electrical charger combines with the male extension to allow a free rotation when mating the wearable electronic device and the external electrical charger before, during, and after a charging of the battery process. An alignment of i) the multiple, arc-shaped, ferrous, metal contacts and the male extension of the wearable electronic device with ii) the magnets in the external electrical charger and the female receptacle of the external electrical charger establishes a flexible coupling between these devices that allows a 360 degree rotation axis for a physical and electrical coupling between the wearable electronic device and the external electrical charger. The 360 degree rotation axis for the physical and electrical coupling is not limited to one or two positional relationships on how these devices couple together before and during the charging process for the battery. The 360 degree mating between charger and the wearable electronic device is enabled before, during, and after charging to allow coupling from virtually all of the different possible mating positions. Because of the 360 degree mechanical alignment between the male extension and the female receptor, then no fixed alignment between the devices is needed.

The external electrical charger using contacts, such as prongs, pins, etc., has three or more magnets to create a pull force to magnetically connect to the caseback portion of the wearable electronic device. The caseback of the wearable electronic device uses ferrous (magnetic) metals to attract the charger and "self connect" to the electrical charger in a proper alignment to conduct the subsequent electrical charging of the battery of the wearable electronic device. In an embodiment, the multiple, arc-shaped, ferrous, metal contacts use the ferrous metals to attract and create a pull force of at least 150 grams to the magnets of the external electrical charger to establish a proper alignment to conduct a subsequent electrical charging of the battery of the wearable electronic device. The pull force may also be, for example, between 200 grams to 140 grams. The pull force/magnetic force can be a measure of an amount attractive force from a magnet to a ferrous material. Thus, the multiple, arc-shaped, ferrous, metal contacts in the wearable electronic device and the three or more magnets spatially located inside the charger use the pull force of at least 150 grams to charge and recharge the wearable electronic device with a 360 degree rotation and improved user experience, via magnetic coupling to self-connect the metal contacts with the prongs of the charger in a proper alignment.

Note, the electrical charger can merely require that the metal contacts comes in close proximity of the prongs of the charger but in most cases a direct contact between these will be made.

In an embodiment, by utilizing multiple, e.g. two or four, concentric contact rings on the wearable electronic device, in combination with magnetic forces hold the charger centered to the watch's back side. The mechanical extension/bump of the heart rate dome and the concentric ring design of the ferrous metal contacts provide a user experience of an electrical charging with a 360 degree rotation/magnetic attraction and centering, and with a speed and an efficiency of a contact charging such as a full charge in less than an hour. The charger itself essentially retains the familiar prongs, (e.g. pins, pads, etc.) but the prongs are spring loaded to adjust to terrain of the caseback's surface. The mechanical and magnetic coupling allow an ease of use where the user does not need to search for contact pins and/or specific alignment to mate these devices. Instead the spatial placing of the magnets and the mechanical oval shapes of the dome and female receptacle essentially automatically align regardless of angle orientation between watch and charger.

Overall, the arc-shaped, ferrous, metal contacts can take the form of, e.g., two or more concentric metal contact rings on a surface of the wearable electronic device, which in combination with the magnets located in the external electrical charger are configured to magnetically to couple the charging pins in the external electrical charger. The male extension extending from the surface of the caseback coupling with the female receptor of the external electrical charger is configured to mechanically couple the external electrical charger to the wearable electronic device. The mechanical coupling and the magnetic coupling creates an alignment in the three dimensions, the Z axis, the X axis, and the Y axis to allow a sufficient level of electrical current charge exchanged from the external electrical charger to the battery of the wearable electronic device to charge the battery from 0 to 100% to occur in less than sixty minutes while maintaining an external surface temperature around the concentric metal contact rings of no greater than 95 degrees F. Thus, the contact rings' temperature will naturally heat up during the charge but will not heat to greater than 95 degrees F. so if the user puts the wearable electronic device on during or immediately after a charge, they will not be burned by the metal contact rings.

Again, since a tight coupling exists between the prongs of the charger and the contacts of the caseback, the amount of charge exchanged from the electrical charger to the battery of the wearable electronic device is significantly increased. Therefore, the time to charge the battery to full capacity is significantly reduced. For example, a full charge from 0 to 100% may occur in about an hour or less, (e.g. 30-31 minutes) while maintaining an external surface temperature around the metal contacts of no greater than 100 degrees F.

Figure 5:
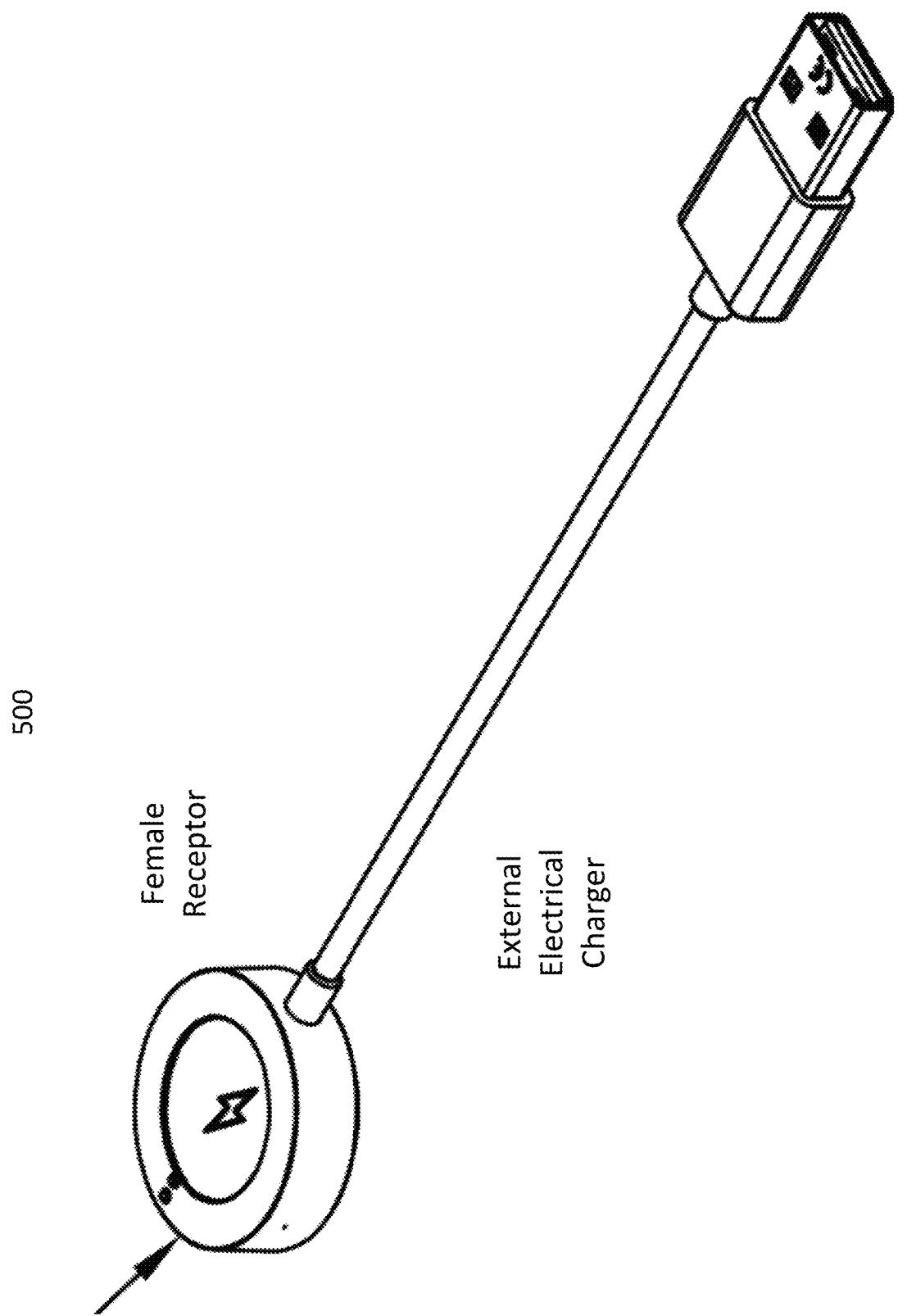
FIG. 5 and FIG. 6 illustrate an embodiment of diagrams of the external electrical charger having an indented female receptacle and pogo pins for charging.
Figure 6:
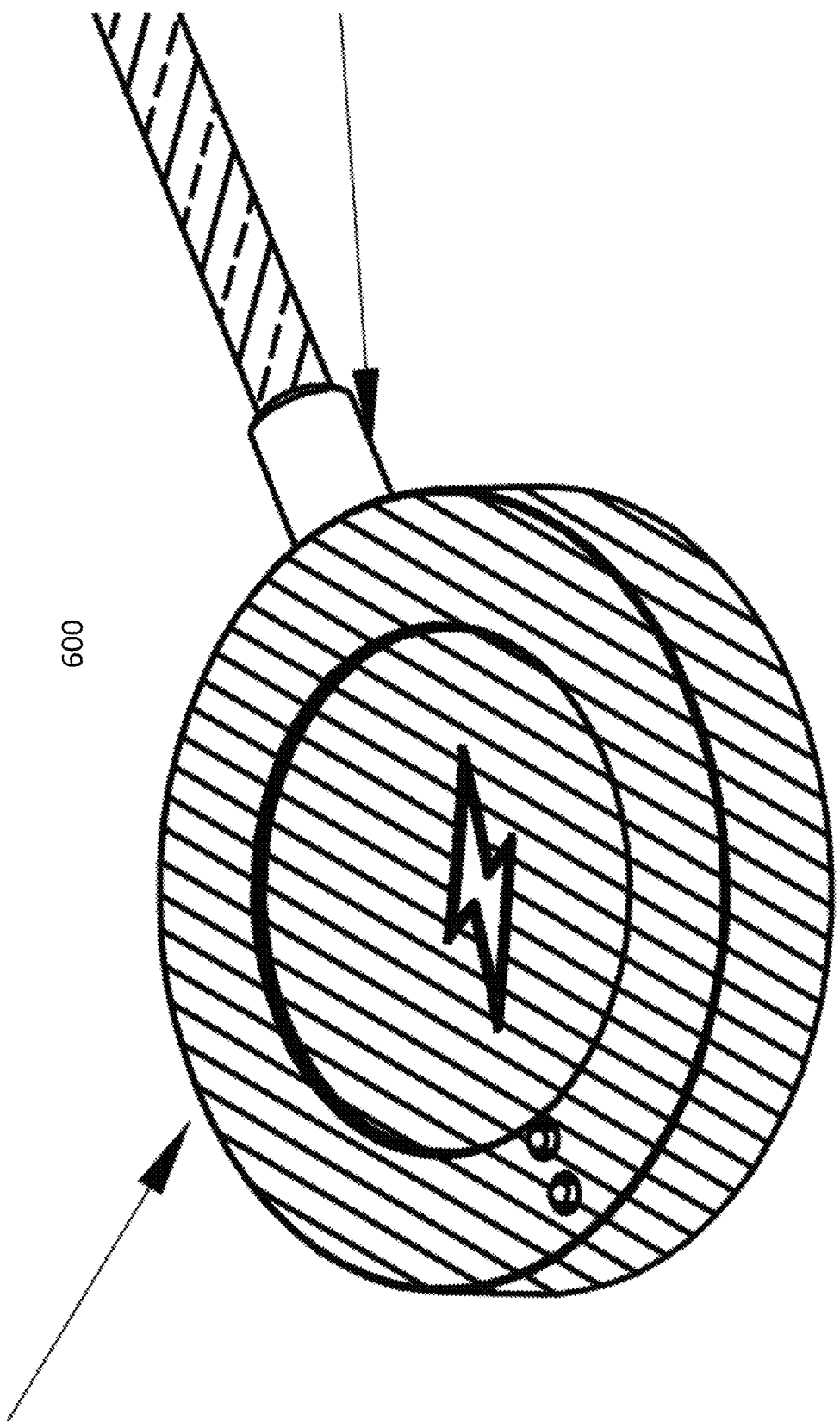

FIG. 5 and FIG. 6 illustrate an embodiment of diagrams of the external electrical charger having an indented female receptacle and pogo pins for charging. The example, pogo pins make a physical connection extend from the charger to the metal contacts on surface of the wearable device. The external electrical charger has an indented female receptacle in the electrical charger in which the male extension may easily mechanically seat into.

Figure 10:
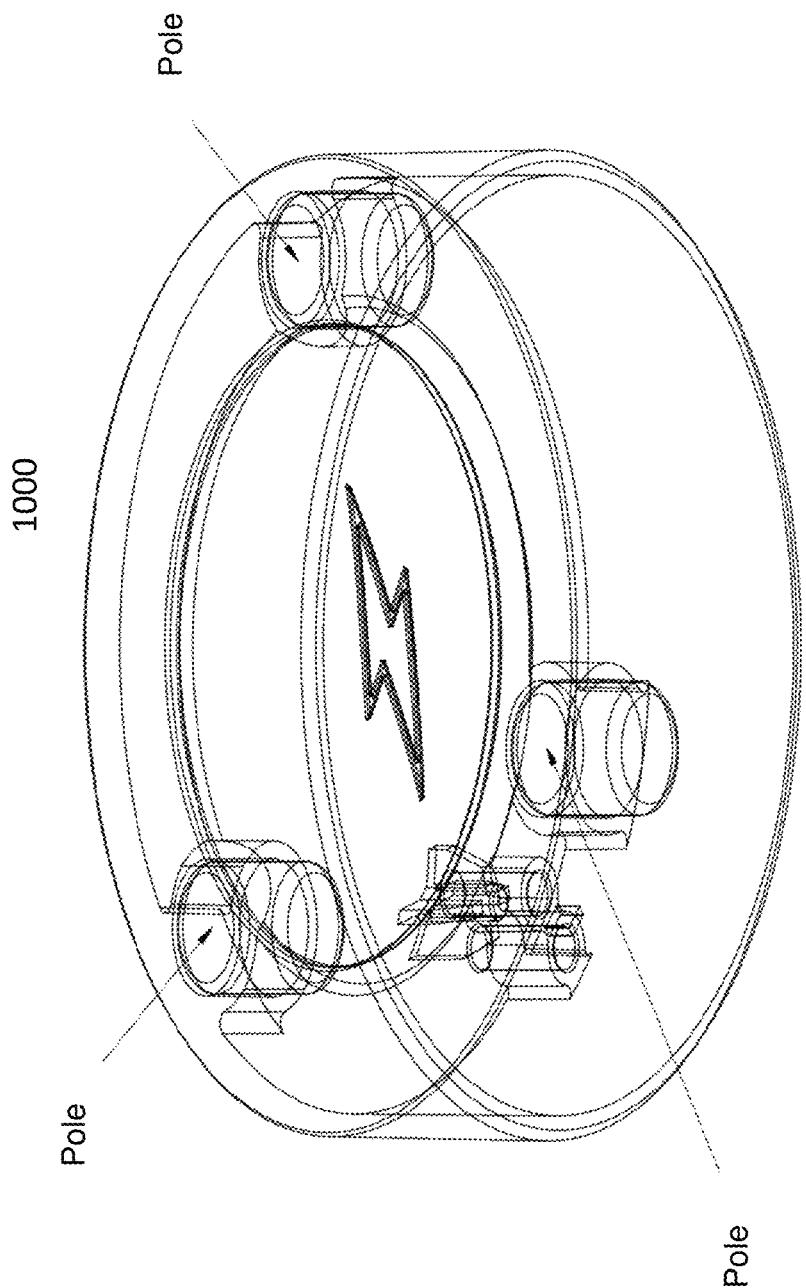
FIG. 10 illustrates a diagram of an embodiment of example magnets located spatially positioned around a center of the external electrical charger.

FIG. 10 illustrates a diagram of an embodiment of example magnets located spatially positioned around a center of the external electrical charger. Multiple magnetics, such as three or more magnetics, located under the surface of the charger, assist in making the magnetic coupling between electrical contacts on the surface of the smart watch and the electrical charger. Each magnet is spatially positioned around the charger to make an tight coupling from that arc/quadrant/region of the connection between the wearable device and the electrical charger.

Referring back to FIG. 4, a magnetic "click" feature can give confidence of a proper alignment between the charger and the wearable device. Also, the wearable device on the display screen may have an icon or other indication in a user interface indicating a battery charge is occurring when the display is activated, as well as, a LED may illuminate on the charger to confirm charging is occurring.

Figure 11A:
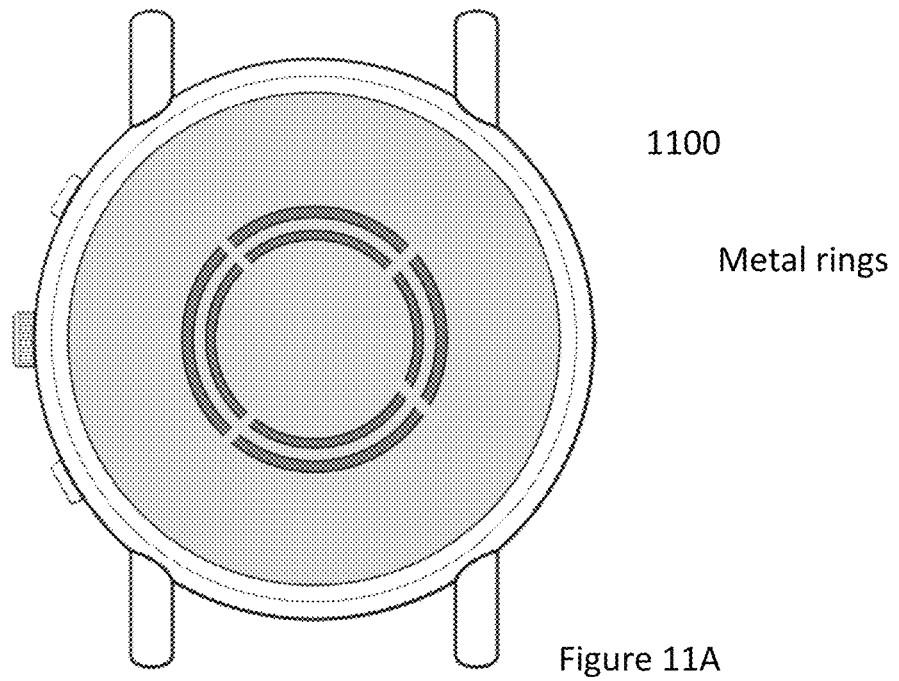
FIGS. 11A and 11B illustrate embodiments of diagrams of different casebacks having different layouts of multiple, arc-shaped, ferrous, metal contacts.
Figure 11B:
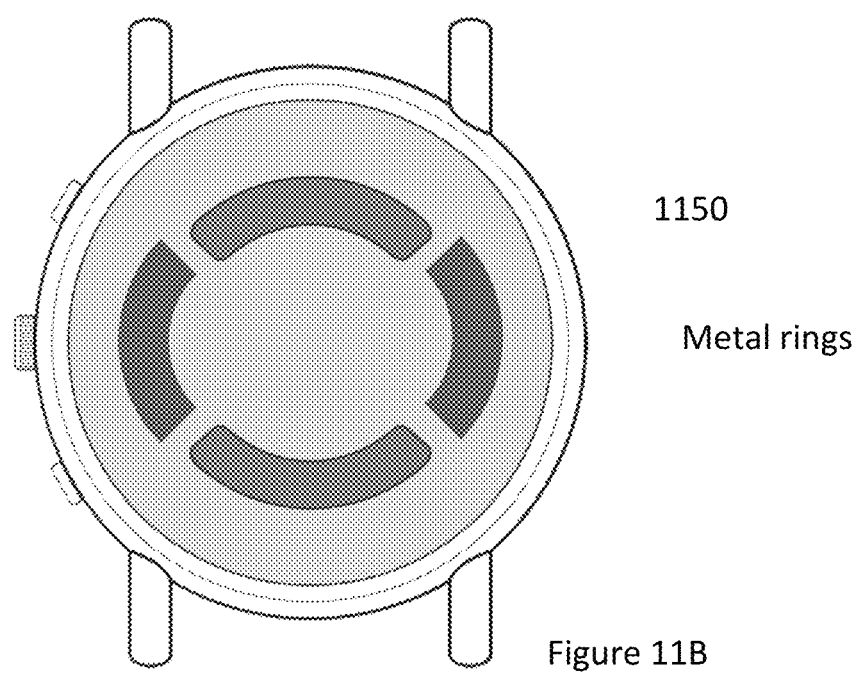

FIGS. 11A and 11B illustrate embodiments of diagrams of different casebacks having different layouts of multiple, arc-shaped, ferrous, arc-shaped, ferrous, metal contacts. Note, the male extensions are not shown in these diagrams.

Next, referring to FIG. 3, i) an overload circuit in the wearable electronic device and ii) one or more water seals in the caseback cooperate to maintain a water proofness to at least three atmospheres, such as 5 ATMs, by merely needing a water seal for each of the arc-shaped, ferrous, metal contacts penetrating the surface of the wearable electronic device. The wearable electronic device maintains water proofness by merely needing a water seal for each mechanical contact penetrating to the surface of the wearable in combination with the overload circuit to electrically open up the electrical circuit between the battery and the exposed surface contacts when the circuit senses either no contact from a contact proximity sensor for the wearable device or when an electrical short condition is detected. The wearable electronic device also uses a variety of water resistant rings to seal the watch to ensure the specific water proofness rating desired is achieved.

In alternative embodiments, the waterproof material prevents water molecules from penetrating through its layered composite fabric when compressed up to 1 atm, 4 atms, 5 atms or more or waterproof and/or water resistant to level 1 of the IPX liquid intrusion table, level 2, level 3, level 4, level 5, level 6, level 7, level 8 or up to level 9K.

Figures 7A, 7B:
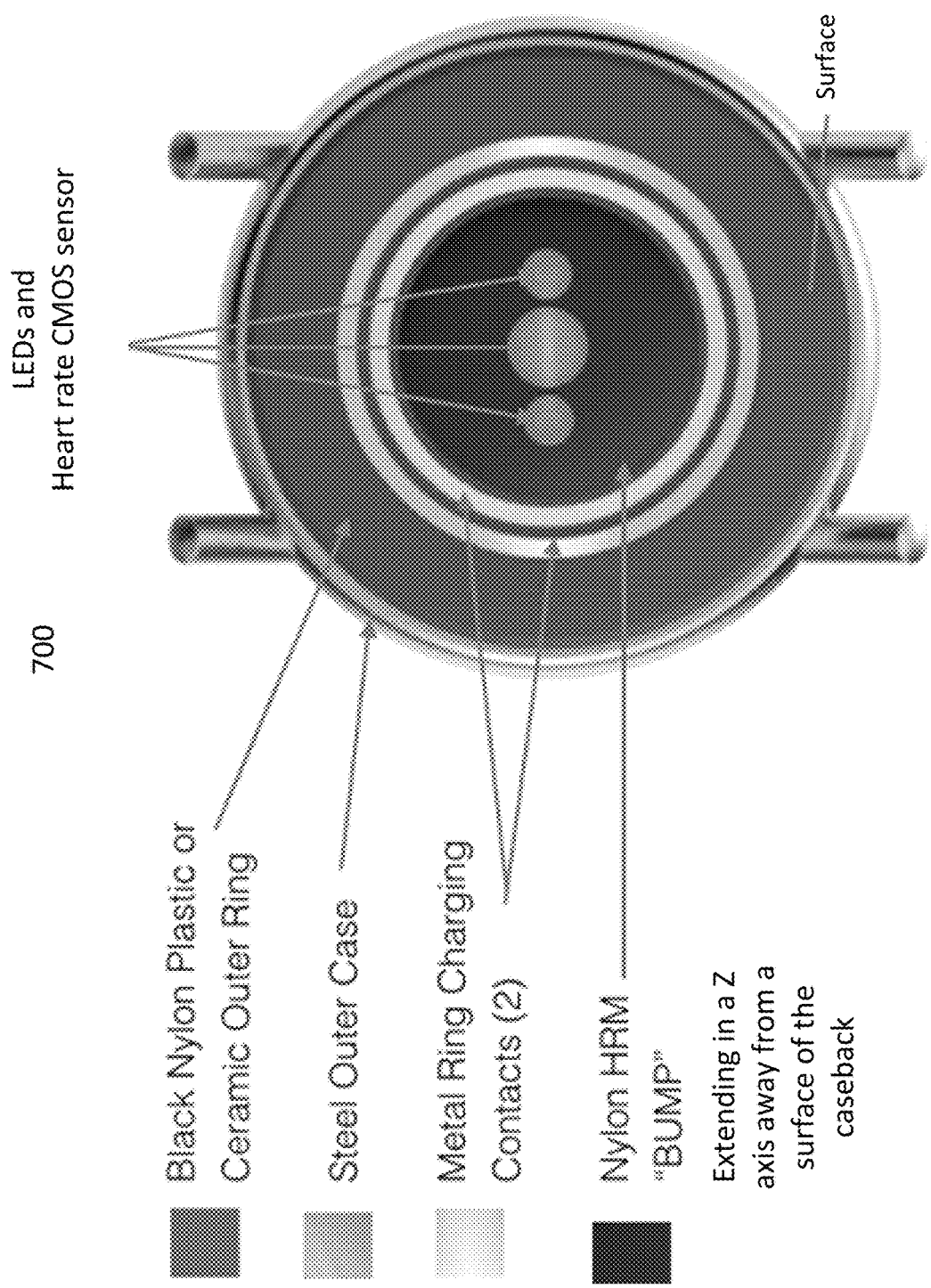
FIGS. 7A and 7B illustrate diagrams of an embodiment of a male extension extending from a surface of the caseback and sets of concentric rings.

FIGS. 7A and 7B illustrate diagrams of an embodiment of a male extension extending from a surface of the caseback and its set of concentric rings. The metal contacts may be made out a corrosion resistant metal that retain magnetic ferrous properties such as 304 or 400 stainless steel, etc. The metal contacts are metal inserts on the surface of and/or through the plastic or ceramic material making up the bulk of the caseback. In an embodiment, the metal contacts may be slightly recessed from the surface. In an embodiment, the metal contacts of the wearable device are slight raised off the surface of the wearable device. In an embodiment, the plastic or ceramic caseback is integrated into the rest of the plastic case of the wearable device, where positionally the charging metal rings are the light colored circles and the male extension is the black assembly with the LEDs and clear light sensors in the center.

Figure 8:
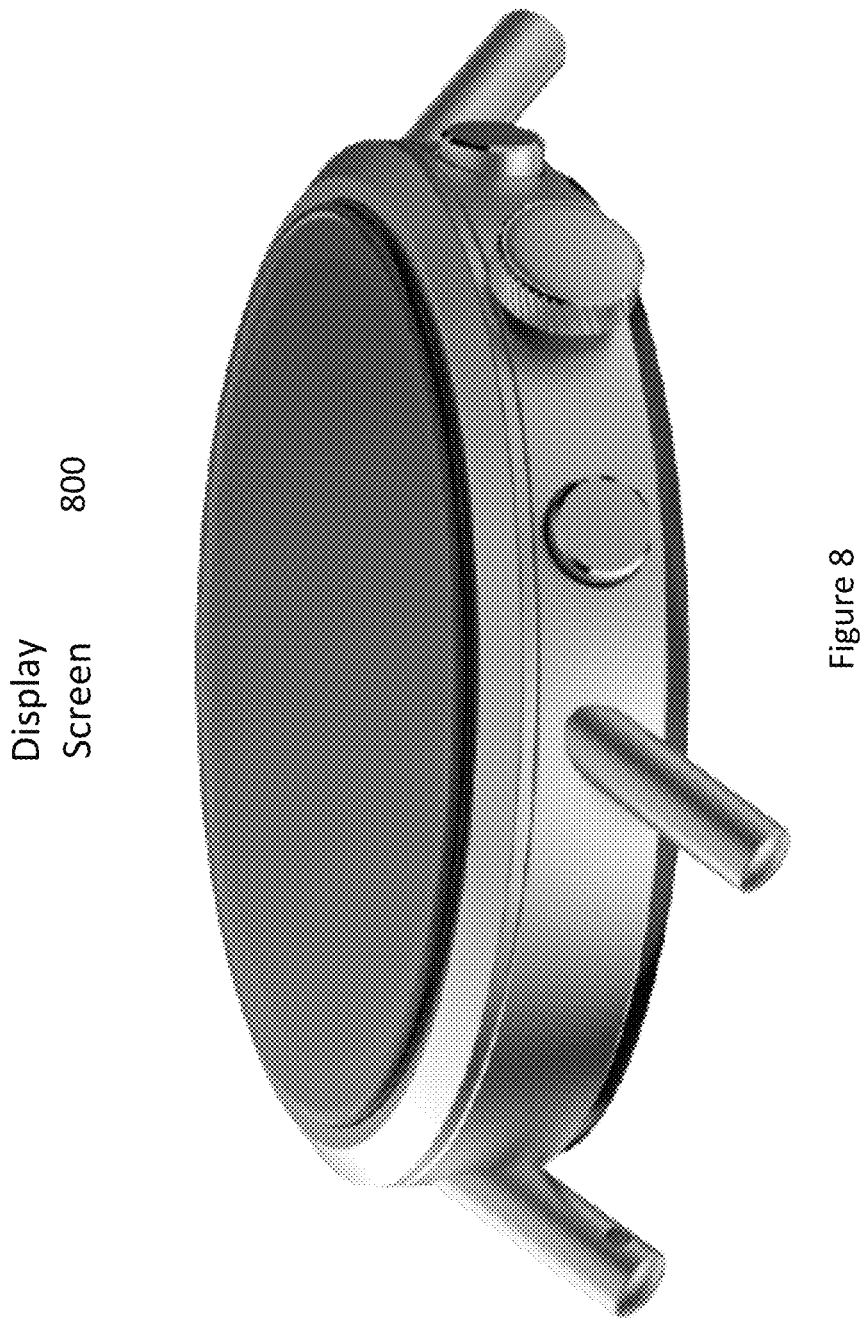
FIG. 8 illustrates a diagram of an embodiment of an example wearable electronic device having a display, one or more processors, one or more memories, one or more batteries, and a caseback.

FIG. 8 illustrates a diagram of an embodiment of an example wearable electronic device having a display, one or more processors, one or more memories, one or more batteries, and a caseback. The wearable electronic device may include various components including a housing with a display screen. One or more processors are located in the housing. The processor is configured to process commands to present an onscreen display on the display screen to enable the wearer of the electronic device to select a number of different operations. One or more non-transitory computer readable storage mediums in the housing are accessible to the processor for storing instructions executable by the processor to generate the number of different operations on the onscreen display. A communication circuit is located in the housing. The communication circuit is configured to transmit wirelessly, such as Bluetooth, Zigbee, Cellular, Wi-Fi, etc. to another computing device cooperating with the wearable electronic device. One or more rechargeable batteries are used for the wearable electronic device. The watch may display electronic hands and/or may have mechanical hands.

Again, the wearable electronic device may be a smart watch or smart activity tracker. The caseback may be used with any wrist worn electronic device requiring an electrical or data based connection with a need for freedom to rotate when electrically coupling. For example, an Analog quartz watch with small screen may also use the caseback with the concentric ring to charge its battery. The watch may use NFC communications (active and passive), use GPS, and possibly have cellular connectivity (e.g. 3G/4G/5G/).

Figure 9:
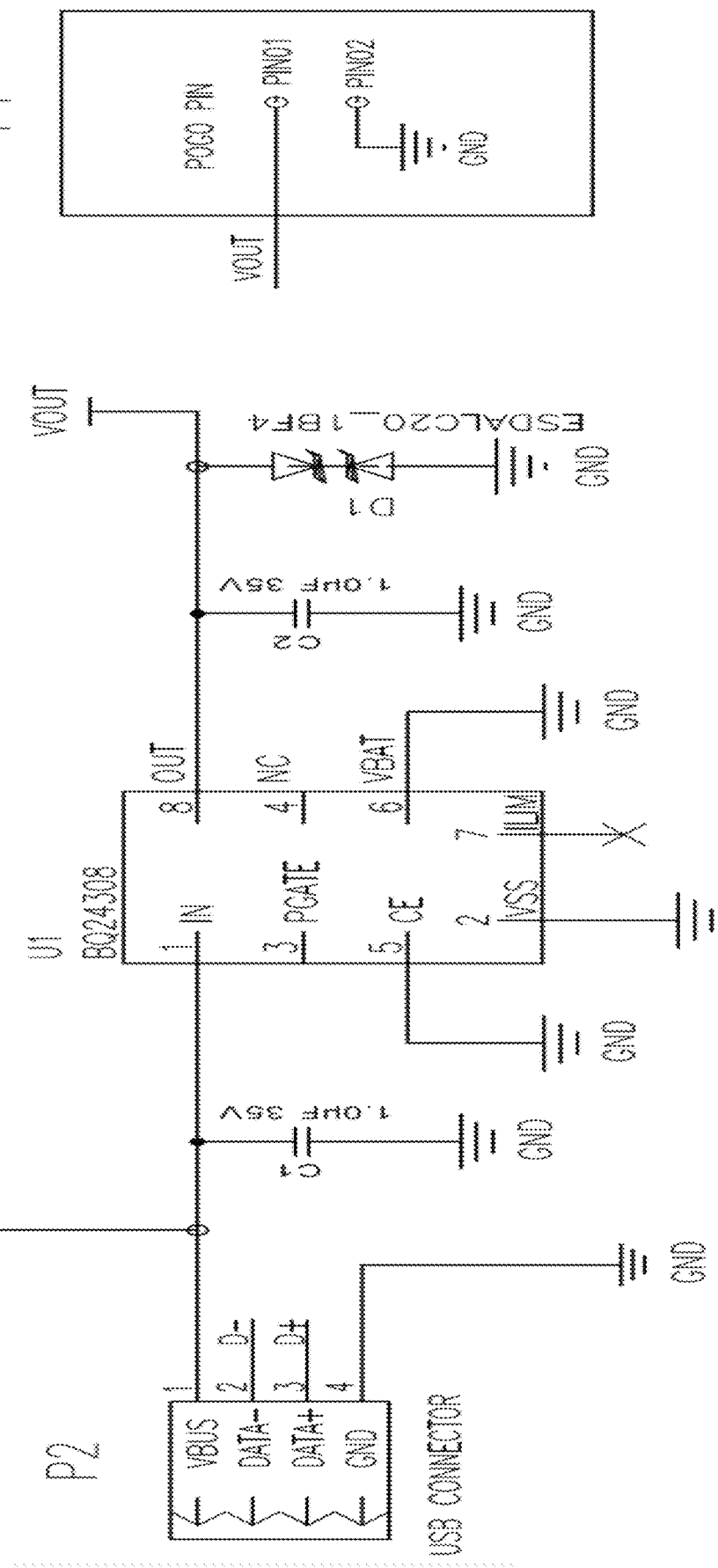
FIG. 9 illustrates a diagram of an embodiment of an example overload circuit in the wearable electronic device configured to prevent a flow of electrical current between the arc-shaped, ferrous, metal contacts going to a rest of a battery circuit in the wearable electronic device when the electrical current equals or exceeds a set point for a maximum input current.

FIG. 9 illustrates a diagram of an embodiment of an example overload circuit located inside the wearable electronic device that is configured to prevent a flow of electrical current between the arc-shaped, ferrous, metal contacts going to a rest of a battery circuit in the wearable electronic device when the electrical current equals or exceeds a set point for a maximum input current. Note, a similar overload circuit may be employed in the external electrical charger. The caseback has multiple electrical contacts in the form of multiple concentric rings made out of a ferrous material, each ring corresponding to a different electrical polarity for the DC charge of the battery. The overload circuit includes a circuit breaking type of device, such as a circuit breaker, an overload diode, an integrated circuit, etc., that electrically opens an electrical circuit from the arc-shaped, ferrous, metal contacts going to the rest of the battery circuit in the wearable electronic device and prevents the electrical current condition that would equal or exceed the maximum input current from harming the battery or other portions of the wearable electronic device. Periodically, the circuit breaking type of device will be re-enabled and when the electrical current condition equals or exceeds the maximum input current remains, then the circuit breaking type of device will again be electrically opened. In an embodiment, the circuit design may include an integrated circuit, such as a T.I. BQ24308 device, which includes the over current protection and the continuous auto-retry features.

The smart wearable device uses a specific overload circuit so that accidental pin touches to an opposite DC electrical polarity a circuit breaking type of device such as a circuit breaker, an overload diode, integrated circuit, etc. electrically opens the electrical circuit from the metal contact going to the rest of the battery circuit in the smart wearable device and does not harm the battery or other portions of the smart wearable device.

The short circuit conditions are expected to occur often with the prongs of the charger and/or the surface contacts of the wearable device. The pogo pins of the charger and or concentric rings of the wearable device which carry USB +5V and Ground are fully exposed with no mechanical protection features. The cable of the external electrical charger includes magnets which may pull unintended magnetic materials into the pogo pins.

The over current protection (OCP) feature allows the charging cable's pogo pins to contact any conductive surface, for any period of time, without damaging the cable or the USB input source (i.e. USB port, or USB AC adapter). Also, once the short circuit condition is removed, the charging cable continues to operate normally after a small delay. The OCP circuit prevents the flow of current when it exceeds the maximum input current specification of the wearable device. In this case, the maximum current that may be drawn by the watch is 500 milliamps. When an over current condition is detected, the output voltage is disabled, and the electrical current falls to 0 mA. Periodically, the output will be reenabled. If the short circuit remains, the output will again be disabled. This auto-retry mechanism occurs continuously until the short circuit is removed, and the output current is no greater than 500 mA.

Figure 12:
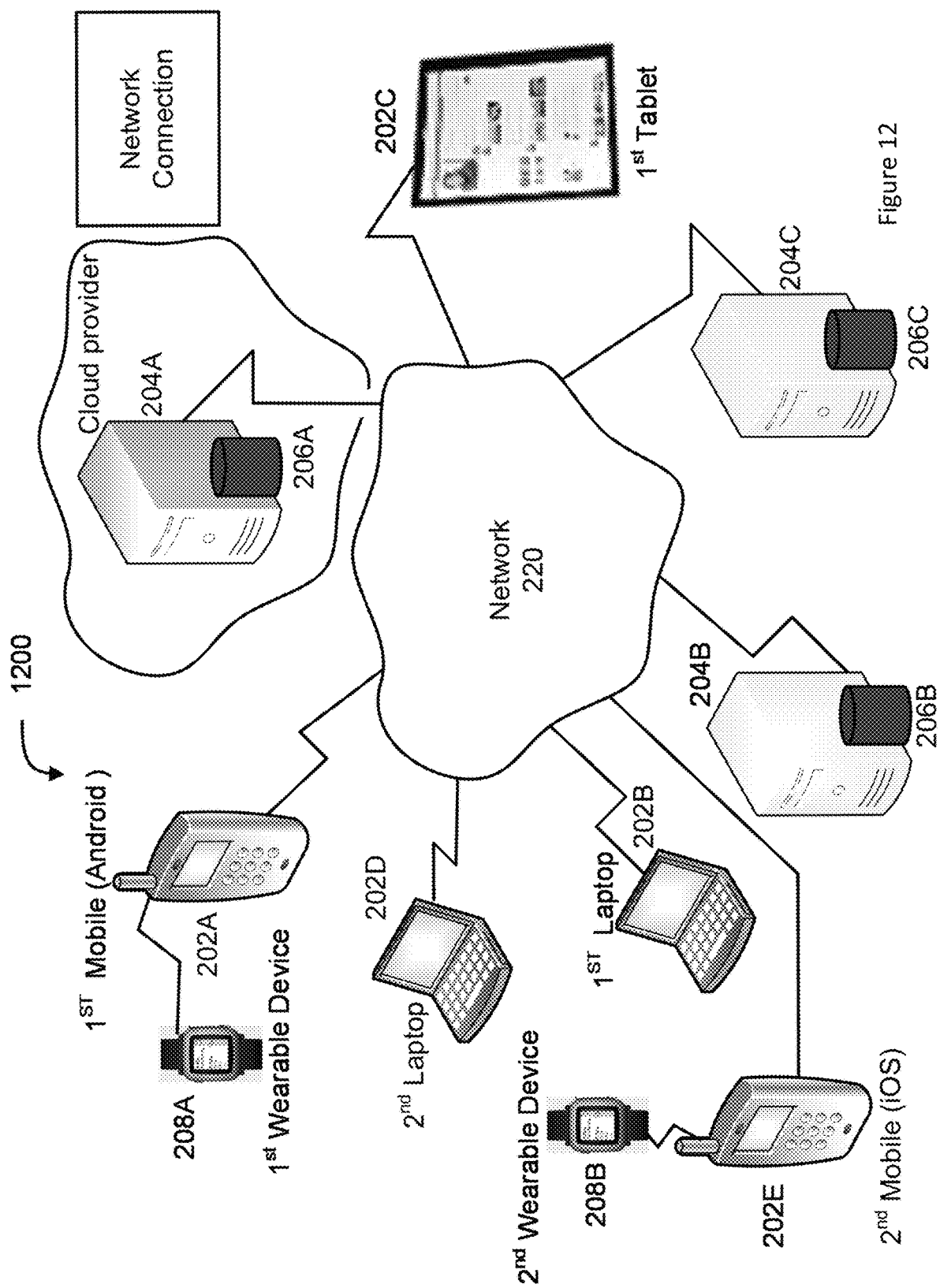
FIG. 12 illustrates a diagram of a network environment in which the techniques described herein may be applied.
Figure 13:
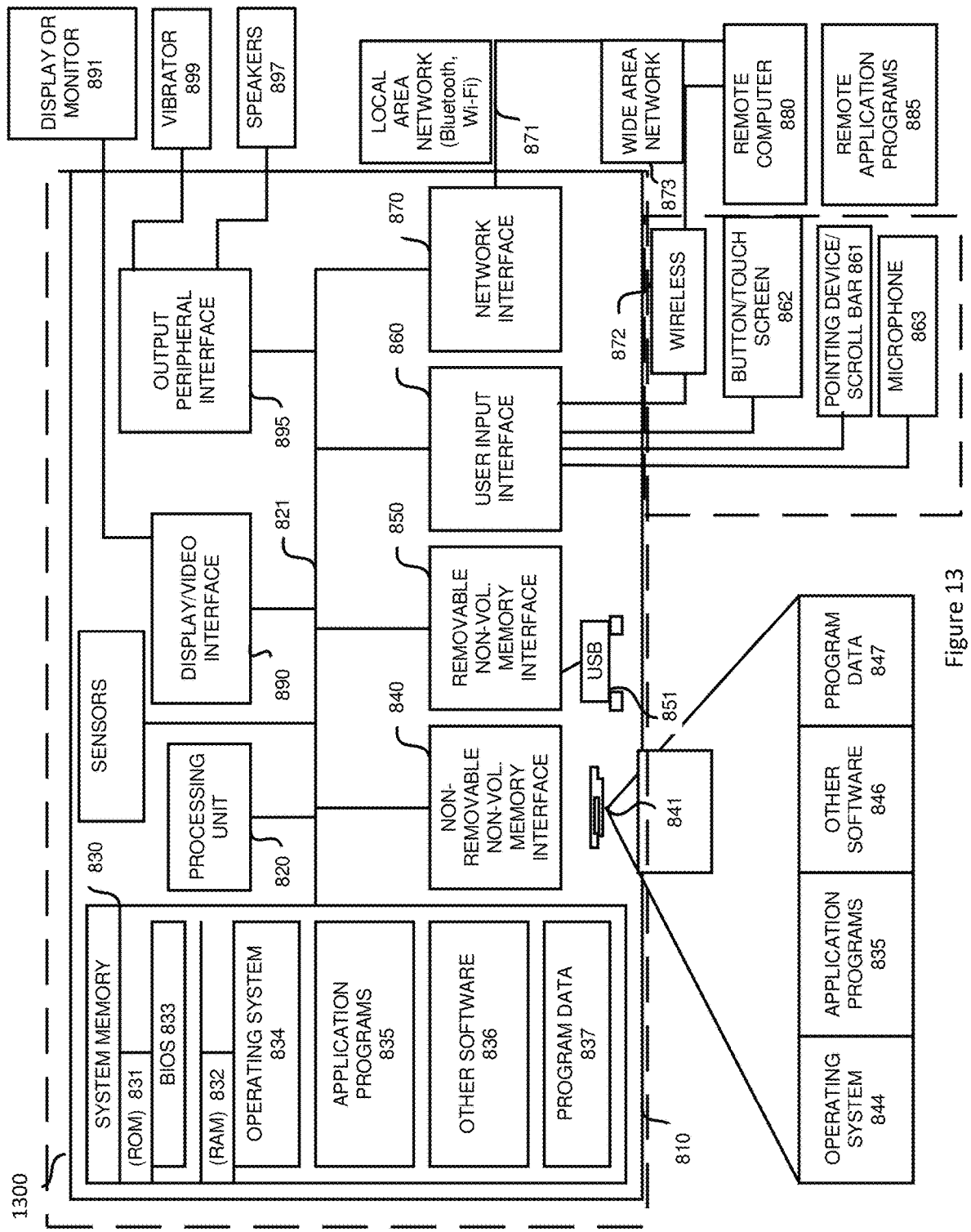
FIG. 13 illustrates a block diagram of an example computing system that may be used in an embodiment of one or more of the servers, the wearable electronic device, and the client devices discussed herein.

In general, the wearable electronic device includes one or more communication and processing systems, which can be coupled externally to one or more networks. FIGS. 12-13 illustrate additional example environments to implement the concepts. The housing also has a computer readable storage medium in the housing accessible to the processor for storing instructions executable by the processor to generate the number of different operations on the onscreen display.

FIG. 13 illustrates a block diagram of an example computing system that may be used in an embodiment of one or more of the servers, a wearable electronic device, and client devices discussed herein. The computing system environment 1300 is only one example of a suitable computing environment, such as a client device, server, wearable electronic device, etc., and is not intended to suggest any limitation as to the scope of use or functionality of the design of the computing system 810. Neither should the computing environment 1300 be interpreted as having any dependency or requirement relating to any one or combination of components illustrated in the exemplary operating environment 1300.

In an embodiment, the wearable electronic device can connect through a wireless network to an app store having thousands of applications and watchfaces that can be downloaded. The applications include notifications for emails, calls, text messages & social media activity; stock prices; activity tracking (movement, sleep, estimates of calories burned); remote controls for smartphones, cameras & home appliances; turn-by-turn directions (using the GPS receiver in a smartphone or tablet); display of RSS or JSON feeds; and also include hundreds of custom watch faces.

In an embodiment, the wearable electronic device can originally be shipped with applications pre-installed. These applications can use data received from a connected phone for distance, speed and range information. The applications can also directly connect to a backend server on the cloud. More applications are downloadable via a mobile phone or tablet.

In an embodiment, the wearable electronic device can integrates with any phone or tablet application that sends out native iOS or Android notifications.

The wearable electronic device also has a computer readable storage medium, e.g., solid-state memory 840, in the housing accessible to the processor 820 and stores instructions executable by the processor to generate the number of different operations on the onscreen display 891.

In an embodiment, the wearable electronic device is a wristwatch that has a watch housing in which the onscreen display bears a time indication, either digital or analog. In certain instances, the wristwatch may be a smart watch. In one embodiment, the wristwatch has one or more manipulatable physical buttons that are arranged on the housing of the watch. In other embodiments, the wristwatch may have a touch screen, scrolling device, additional buttons or a combination of some or all of these. A flexible wristband is engagable with the housing of the watch to hold the housing of the watch onto a wearer.

In an embodiment, the electronic wearable device has a bezel coupled to the display screen as well has a lithium based battery. The lithium-based battery is located in the housing. In one embodiment, the lithium-based battery has at least 130 milliampere-hour (mAh) in electrical storage capacity, and can power the electronic components in a wearable electronic device. The lithium-based battery can also power the display screen, the communication circuit, and the processor. The display screen can be selected from the group of any of an ePaper display, a monochrome LCD display, and a color LED backlit display, and OLED display, that all consume lower battery power than some other color LCD screens. The battery contains enough capacity of at least 130 mAh to allow the display screen to stay on constantly and last up to multiple days on a single charge of the battery.

In an embodiment, the wearable electronic device is a smart watch which features a LCD display screen, a programmable CPU, memory, storage, Bluetooth, a vibrating motor, a heart rate sensor, GPS, and an accelerometer. These features extend the smart watch's use beyond just displaying the time on the display screen and into many roles including interacting with smartphone notifications, activity tracking, gaming, map display, golf tracking, and more. The smart watch is compatible with Android and iOS devices. When connected to one of these devices via Bluetooth, the smart watch can (but may not need to) pair with that device and vibrate and display text messages, fitness information, emails, incoming calls, and notifications from social media accounts. The smart watch can also act as a remote control for the telephone function in the paired device, or for other paired devices containing a camera such as the GoPro.

Computing System

With reference to FIG. 13, components of the computing system 810 may include, but are not limited to, a processing unit 820 having one or more processing cores, a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) locale bus, and Peripheral Component Interconnect (PCI) bus.

Computing system 810 typically includes a variety of computing machine-readable media. Computing machine-readable media can be any available media that can be accessed by computing system 810 and includes both volatile and nonvolatile media, removable and non-removable media. By way of example, and not limitation, computing machine-readable mediums uses include storage of information, such as computer readable instructions, data structures, other executable software or other data. Computer storage mediums include, but are not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other tangible medium which can be used to store the desired information and which can be accessed by computing device 1300. Transitory media such as wireless channels are not included in the machine-readable media. Communication media typically embodies computer readable instructions, data structures, other executable software, or other transport mechanism and includes any information delivery media. As an example, some clients on network 220 of FIG. 12 may not have any optical or magnetic storage.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computing system 810, such as during start-up, is typically stored in ROM 831. RAM 832 typically contains data and/or software that are immediately accessible to and/or presently being operated on by processing unit 820. By way of example, and not limitation, FIG. 13 illustrates that RAM can include a portion of the operating system 834, other executable software 836, and program data 837.

The computing system 810 may also include other removable/non-removable volatile/nonvolatile computer storage media. By way of example only, FIG. 13 illustrates a solid-state memory 841. Other removable/non-removable, volatile/nonvolatile computer storage media that can be used in the exemplary operating environment include, but are not limited to, USB drives and devices, flash memory cards, solid state RAM, solid state ROM, and the like. The solid-state memory 841 is typically connected to the system bus 821 through a non-removable memory interface such as interface 840, and USB drive 851 is typically connected to the system bus 821 by a removable memory interface, such as interface 850. In an example, the wearable electronic device can have RAM which can include some space for the OS, 24 some space for the applications, and some space for the services.

As an example, the computer readable storage medium 841 stores Operating System software for smart watches to cooperate with both Android OS and iOS.

The drives and their associated computer storage media discussed above and illustrated in FIG. 13, provide storage of computer readable instructions, data structures, other executable software and other data for the computing system 810. In FIG. 13, for example, the solid state memory 841 is illustrated for storing operating system 844, other executable software 846, and program data 847. Note that these components can either be the same as or different from operating system 834, other executable software 836, and program data 837. Operating system 844, other executable software 846, and program data 847 are given different numbers here to illustrate that, at a minimum, they are different copies.

A user may enter commands and information into the computing system 810 through input devices such as a keyboard, touchscreen, or even push button input component 862, a microphone 863, a pointing device and/or scrolling input component 861, such as a mouse, trackball or touch pad. The microphone 863 may cooperate with speech recognition software. These and other input devices are often connected to the processing unit 820 through a user input interface 860 that is coupled to the system bus, but may be connected by other interface and bus structures, such as a parallel port, game port or a universal serial bus (USB). A display monitor 891 or other type of display screen device is also connected to the system bus 821 via an interface, such as a display and video interface 890. In addition to the monitor, computing devices may also include other peripheral output devices such as speakers 897 and other output device, which may be connected through an output peripheral interface 890.

The computing system 810 may operate in a networked environment using logical connections to one or more remote computers/client devices, such as a remote computing device 880. The remote computing device 880 may be a wearable electronic device, a personal computer, a hand-held device, a server, a router, a network PC, a peer device or other common network node, and typically includes many or all of the elements described above relative to the computing system 810. The logical connections depicted in FIG. 13 include a local area network (LAN) 871 and a wide area network (WAN) 873, but may also include other networks. Such networking environments are commonplace in offices, enterprise-wide computer networks, intranets and the Internet. A browser application may be resident on the computing device and stored in the memory.

When used in a LAN networking environment, the computing system 810 is connected to the LAN 871 through a network interface or adapter 870, which can be a Bluetooth or Wi-Fi adapter. When used in a WAN networking environment, the computing system 810 typically includes a modem 872, e.g., a wireless network, or other means for establishing communications over the WAN 873, such as the Internet. The wireless modem 872, which may be internal or external, may be connected to the system bus 821 via the user-input interface 860, or other appropriate mechanism. In a networked environment, other software depicted relative to the computing system 810, or portions thereof, may be stored in the remote memory storage device. By way of example, and not limitation, FIG. 13 illustrates remote application programs 885 as residing on remote computing device 880. It will be appreciated that the network connections shown are exemplary and other means of establishing a communications link between the computing devices may be used.

As discussed, the computing system may include a processor, a memory, a built in battery to power the computing device, an AC power input to charge the battery, a display screen, a built-in Wi-Fi circuitry to wirelessly communicate with a remote computing device connected to network.

It should be noted that the present design can be carried out on a computing system such as that described with respect to FIG. 13. However, the present design can be carried out on a server, a computing device devoted to message handling, or on a distributed system in which different portions of the present design are carried out on different parts of the distributed computing system.

Another device that may be coupled to bus 811 is a power supply such as a battery and Alternating Current adapter circuit. As discussed above, the DC power supply may be a battery, a fuel cell, or similar DC power source that needs to be recharged on a periodic basis. The wireless communication module 872 may employ a Wireless Application Protocol to establish a wireless communication channel. The wireless communication module 872 may implement a wireless networking standard such as Institute of Electrical and Electronics Engineers (IEEE) 802.11 standard, IEEE std. 802.11-1999, published by IEEE in 1999.

Examples of mobile computing devices may be a wearable electronic device, a laptop computer, a cell phone, a personal digital assistant, or other similar device with on board processing power and wireless communications ability that is powered by a Direct Current (DC) power source that supplies DC voltage to the mobile device and that is solely within the mobile computing device and needs to be recharged on a periodic basis, such as a fuel cell or a battery.

Network Environment

FIG. 12 illustrates a diagram of a network environment in which the techniques described herein may be applied. The network environment 1200 has a communications network 220 that connects server computing systems 204A through 204C, and at least one or more client computing systems 202A to 202F. As shown, there may be many server computing systems 204A through 204C and many client computing systems 202A to 202F connected to each other via the network 220, which may be, for example, the Internet. Note, that alternatively the network 220 might be or include one or more of: an optical network, a cellular network, the Internet, a Local Area Network (LAN), Wide Area Network (WAN), satellite link, fiber network, cable network, or a combination of these and/or others. It is to be further appreciated that the use of the terms client computing system and server computing system is for clarity in specifying who generally initiates a communication (the client computing system) and who responds (the server computing system). No hierarchy is implied unless explicitly stated. Both functions may be in a single communicating device, in which case the client-server and server-client relationship may be viewed as peer-to-peer. Thus, if two systems such as the client computing system 202A and the server computing system 204A can both initiate and respond to communications, their communication may be viewed as peer-to-peer. Likewise, communications between the server computing systems 204A and 204-B, and the client computing systems 202A and 202C may be viewed as peer-to-peer if each such communicating device is capable of initiation and response to communication. Additionally, server computing systems 204A-204C also have circuitry and software to communication with each other across the network 220. One or more of the server computing systems 204A to 204C may be associated with a database such as, for example, the databases 206A to 206C. Each server may have one or more instances of a virtual server running on that physical server and multiple virtual instances may be implemented by the design. A firewall may be established between a client computing system 202C and the network 220 to protect data integrity on the client computing system 202C. Each server computing system 204A-204C may have one or more firewalls.

A cloud provider service can install and operate application software in the cloud and users can access the software service from the client devices. Cloud users who have a site in the cloud may not solely manage the cloud infrastructure and platform where the application runs. Thus, the servers and databases may be shared hardware where the user is given a certain amount of dedicate use of these resources. The user's cloud-based site is given a virtual amount of dedicated space and bandwidth in the cloud. Cloud applications can be different from other applications in their scalability which can be achieved by cloning tasks onto multiple virtual machines at run-time to meet changing work demand. Load balancers distribute the work over the set of virtual machines. This process is transparent to the cloud user, who sees only a single access point.

The cloud-based remote access is coded to utilize a protocol, such as Hypertext Transfer Protocol (HTTP), to engage in a request and response cycle with both a mobile device application resident on a client device as well as a web-browser application resident on the client device. The cloud-based remote access for a wearable electronic device, can be accessed by a mobile device, a desktop, a tablet device, and other similar devices, anytime, anywhere. Thus, the cloud-based remote access to a wearable electronic device hosted on a cloud-based provider site is coded to engage in 1) the request and response cycle from all web browser based applications, 2) SMS/twitter based request and response message exchanges, 3) the request and response cycle from a dedicated on-line server, 4) the request and response cycle directly between a native mobile application resident on a client device and the cloud-based remote access to a wearable electronic device, and 5) combinations of these.

In an embodiment, the server computing system 204A may include a server engine, a web page management component, a content management component, and a database management component. The server engine performs basic processing and operating system level tasks. The web page management component handles creation and display or routing of web pages or screens associated with receiving and providing digital content and digital advertisements. Users may access the server-computing device by means of a URL associated therewith. The content management component handles most of the functions in the embodiments described herein. The database management component includes storage and retrieval tasks with respect to the database, queries to the database, and storage of data.

An embodiment of a server computing system to display information, such as a web page, etc. is discussed. An application including any program modules, when executed on the server computing system 204A, causes the server computing system 204A to display windows and user interface screens on a portion of a media space, such as a web page. A user via a browser from the client computing system 202A may interact with the web page, and then supply input to the query/fields and/or service presented by a user interface of the application. The web page may be served by a web server computing system 204A on any Hypertext Markup Language (HTML) or Wireless Access Protocol (WAP) enabled client computing system 202A or any equivalent thereof. For example, the client mobile computing system 202A may be a wearable electronic device, smart phone, a touch pad, a laptop, a netbook, etc. The client computing system 202A may host a browser to interact with the server computing system 204A. Each application has a code scripted to perform the functions that the software component is coded to carry out such as presenting fields and icons to take details of desired information. Algorithms, routines, and engines within the server computing system 204A take the information from the presenting fields and icons and put that information into an appropriate storage medium such as a database. A comparison wizard is scripted to refer to a database and make use of such data. The applications may be hosted on the server computing system 204A and served to the browser of the client computing system 202A or directly to an app running on the client computing system 202A. The applications then serve pages that allow entry of details and further pages that allow entry of more details.

Scripted Code

Any application and other scripted code components may be stored on a non-transitory computing machine-readable medium which, when executed on the machine causes the machine to perform those functions. The applications including program modules may be implemented as logical sequences of software code, hardware logic circuits, and any combination of the two, and portions of the application scripted in software code are stored in a non-transitory computing device readable medium in an executable format.

In an embodiment, the hardware logic consists of electronic circuits that follow the rules of Boolean Logic, software that contain patterns of instructions, or any combination of both.

The design is also described in the general context of computing device executable instructions, such as applications etc. being executed by a computing device. Generally, programs include routines, objects, widgets, plug-ins, and other similar structures that perform particular tasks or implement particular abstract data types. Those skilled in the art can implement the description and/or figures herein as computer-executable instructions, which can be embodied on any form of computing machine-readable media discussed herein.

Some portions of the detailed descriptions herein are presented in terms of algorithms/routines and symbolic representations of operations on data bits within a computer memory. These algorithmic descriptions and representations are the means used by those skilled in the data processing arts to most effectively convey the substance of their work to others skilled in the art. An algorithm/routine is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. These algorithms/routine of the application including the program modules may be written in a number of different software programming languages such as C, C++, Java, HTML, or other similar languages.

It should be borne in mind, however, that all of these and similar terms are to be associated with the appropriate physical quantities and are merely convenient labels applied to these quantities. Unless specifically stated otherwise as apparent from the above discussions, it is appreciated that throughout the description, discussions utilizing terms such as "processing" or "computing" or "calculating" or "determining" or "displaying" or the like, refer to the action and processes of a computing system, or similar electronic computing device, that manipulates and transforms data represented as physical (electronic) quantities within the computing system's registers and memories into other data similarly represented as physical quantities within the computing system memories or registers, or other such information storage, transmission or display devices.

Although embodiments of this design have been fully described with reference to the accompanying drawings, it is to be noted that various changes and modifications will become apparent to those skilled in the art. Such changes and modifications are to be understood as being included within the scope of embodiments of this design as defined by the appended claims. For example, the device may include a barometer inside the housing of the device that also makes use of the microphone sealing component with one or more channels with the water resistant material for reasons of mechanical robustness as well as the pressure equalization benefit. Alternatively, the device may act as a barometer with the microphone seal with one or more channels to allow the sensed pressure internally in the device, the device uses this internal pressure to detect current depth of the device by the pressure. The invention is to be understood as not limited by the specific embodiments described herein, but only by scope of the appended claims.

What is claimed is:

1. An apparatus, comprising:
a caseback for a wearable electronic device, where the caseback has
multiple, arc-shaped, ferrous, metal contacts that serve a dual purpose of i) establishing a physical electrical input connection between a battery for the wearable electronic device and charging prongs of an external electrical charger and ii) establishing a magnetic coupling between the wearable electronic device and multiple magnets in the external electrical charger to hold the metal contacts of the wearable electronic device and the charging prongs of the external electrical charger in place during a charging of the battery for the wearable electronic device; and
a male extension extending from a surface of the caseback to couple into a female receptor of the external electrical charger, where i) the multiple, arc-shaped, ferrous, metal contacts' relationship with a positioning of the magnetics in the external electrical charger in combination with ii) the male extension of the caseback coupling into the female receptor of the external electrical charger use magnetic and mechanical coupling to establish and control an alignment of the metal contacts with the charging prongs in three dimensions, a Z axis, an X axis, and a Y axis.

2. The apparatus of claim 1, where an alignment of i) the multiple, arc-shaped, ferrous, metal contacts and the male extension of the wearable electronic device with ii) the magnets in the external electrical charger and the female receptacle of the external electrical charger establishes a flexible coupling between these devices that allows a 360 degree rotation axis for a physical and electrical coupling between the wearable electronic device and the external electrical charger, where the 360 degree rotation axis for the physical and electrical coupling is not limited to one or two positional relationships on how these devices couple together before and during a charging process for the battery.

3. The apparatus of claim 1, where the external electrical charger has three or more magnets located inside the charger to magnetically connect to the caseback, where the multiple, arc-shaped, ferrous, metal contacts use the ferrous metals to attract and create a pull force of at least 150 grams to the magnets of the external electrical charger to establish a proper alignment to conduct a subsequent electrical charging of the battery of the wearable electronic device.

4. The apparatus of claim 1, where the male extension creates a mechanical 'male-female' seating with a matching shaped female receptor in the external electrical charger, where the male extension takes the form and shape of a curved dome rising in the Z direction from the surface plane of the caseback, where the curved dome spans merely a portion of the surface plane of the caseback and does not extend for an entire length of the caseback, and the parts of the caseback are made of i) ceramic, ii) plastic, or iii) a combination of both.

5. The apparatus of claim 1, further comprising:
an overload circuit in the wearable electronic device configured to prevent a flow of electrical current between the arc-shaped, ferrous, metal contacts going to a rest of a battery circuit in the wearable electronic device when the electrical current equals or exceeds a set point for a maximum input current, where the overload circuit includes a circuit breaking type of device that electrically opens an electrical circuit from the arc-shaped, ferrous, metal contacts going to the rest of the battery circuit in the wearable electronic device and prevents the electrical current condition that would equal or exceed the maximum input current from harming the battery or other portions of the wearable electronic device, where periodically, the circuit breaking type of device will be re-enabled and when the electrical current condition equaling or exceeding the maximum input current remains, then the circuit breaking type of device will again be electrically opened.

6. The apparatus of claim 1, further comprising:
a heart rate sensor in the wearable electronic device, where the heart rate sensor is electrically connected to the battery, where the wearable electronic device is a smart watch;
where the arc-shaped, ferrous, metal contacts take the form of either i) two or ii) four concentric metal contact rings in the caseback, and then in combination with the magnets located spatially positioned around a center of the external electrical charger are used to magnetically hold the charger prongs of the external electrical charger to the caseback side of the smart watch; and
where the male extension extending from the surface of the caseback is a mechanical oval dome housing the heart rate sensor, and the concentric metal contact rings and mechanical oval dome mate to the external electrical charger to combine to provide a user experience with the external electrical charger to achieve a 360 degree rotation between the concentric metal contact rings and the charger prongs via magnetic attraction, mechanical coupling, and centering.

7. The apparatus of claim 5, where the overload circuit and one or more water seals in the wearable electronic device cooperate to maintain a water proofness to at least three atmospheres by needing a water seal for each of the arc-shaped, ferrous, metal contacts penetrating the surface of the wearable electronic device.

8. The apparatus of claim 1, where the arc-shaped, ferrous, metal contacts take the form of two or more concentric metal contact rings on a surface of the wearable electronic device, which in combination with the magnets located in the external electrical charger are configured to magnetically to couple the charging pins in the external electrical charger, and where the male extension extending from the surface of the caseback coupling with the female receptor of the external electrical charger is configured to mechanically couple the external electrical charger to the wearable electronic device, where the mechanical coupling and the magnetic coupling creates an alignment in the three dimensions, the Z axis, the X axis, and the Y axis to allow a sufficient level of electrical current charge exchanged from the external electrical charger to the battery of the wearable electronic device to charge the battery from 0 to 100% to occur in less than sixty minutes while maintaining an external surface temperature around the concentric metal contact rings of no greater than 95 degrees F.

9. The apparatus of claim 1, where the male extension has an oval shape and a corresponding matching oval depression in the female receptor of the external electrical charger that allow a free rotation when mating the wearable electronic device and the external electrical charger before and during the charging of the battery process.

10. A method of manufacturing for a caseback, comprising:
making the caseback for a wearable electronic device, where the caseback has
multiple, arc-shaped, ferrous, metal contacts that serve a dual purpose of i) establishing a physical electrical input connection between a battery for the wearable electronic device and charging prongs of an external electrical charger and ii) establishing magnetic coupling between the wearable electronic device and multiple magnets in the external electrical charger to hold the metal contacts of the wearable electronic device and the charging prongs of the external electrical charger in place during a charging of the battery for the wearable electronic device; and making a male extension extending from a surface of the caseback to couple into a female receptor of the external electrical charger, where the multiple, arc-shaped, ferrous, metal contacts' relationship with a positioning of the magnetics in the external electrical charger in combination with the male extension of the caseback coupling into the female receptor of the external electrical charger are magnetically and mechanically configured to establish and control an alignment of the metal contacts with the charging prongs of the external electrical charger in three dimensions, a Z axis, an X axis, and Y axis.

11. The method of claim 10, where an alignment of i) the multiple, arc-shaped, ferrous, metal contacts and the male extension of the wearable electronic device with ii) the magnets in the external electrical charger and the female receptacle of the external electrical charger establishes a flexible coupling between these devices that allows a 360 degree rotation axis for a physical and electrical coupling between the wearable electronic device and the external electrical charger, where the 360 degree rotation axis for the physical and electrical coupling is not limited to one or two positional relationships on how these devices couple together before and during the charging process for the battery.

12. The method of claim 10, where the male extension has an oval shape and a corresponding matching oval depression in the female receptor of the external electrical charger that allow a free rotation when mating the wearable electronic device and the external electrical charger before and during the charging of the battery process.

13. The method of claim 10, where the external electrical charger has three or more magnets located inside the charger to magnetically connect to the caseback, where the multiple, arc-shaped, ferrous, metal contacts use the ferrous metals to attract and create a pull force of at least 150 grams to the magnets of the external electrical charger to establish a proper alignment to conduct a subsequent electrical charging of the battery of the wearable electronic device.

14. The method of claim 10, where the male extension creates a mechanical 'male-female' seating with a matching shaped female receptor in the external electrical charger, where the male extension takes the form and shape of a curved dome rising in the Z direction from the surface plane of the caseback, where the curved dome spans merely a portion of the surface plane of the caseback and does not extend for an entire length of the caseback, and the parts of the caseback are made of i) ceramic, ii) plastic, or iii) a combination of both.

15. The method of claim 10, further comprising:
an overload circuit in the wearable electronic device configured to prevent a flow of electrical current between the arc-shaped, ferrous, metal contacts going to a rest of a battery circuit in the wearable electronic device when the electrical current equals or exceeds a set point for a maximum input current, where the overload circuit includes a circuit breaking type of device that electrically opens an electrical circuit from the arc-shaped, ferrous, metal contacts going to the rest of the battery circuit in the wearable electronic device and prevents the electrical current condition that would equal or exceed the maximum input current from harming the battery or other portions of the wearable electronic device, where periodically, the circuit breaking type of device will be re-enabled and when the electrical current condition equaling or exceeding the maximum input current remains, then the circuit breaking type of device will again be electrically opened.

16. The method of claim 10, further comprising:
a heart rate sensor in the wearable electronic device, where the heart rate sensor is electrically connected to the battery, where the wearable electronic device is a smart watch;

where the arc-shaped, ferrous, metal contacts take the form of either i) two or ii) four concentric metal contact rings on the surface of the caseback, and then in combination with the magnets located spatially positioned around a center of the external electrical charger are used to magnetically hold the charger prongs of the external electrical charger to the caseback side of the smart watch; and where the male extension extending from the surface of the caseback is a mechanical oval dome housing the heart rate sensor, and the concentric metal contact rings and mechanical oval dome mate to the external electrical charger to combine to provide a user experience with the external electrical charger to achieve a 360 degree rotation between the concentric metal contact rings and the charger prongs via magnetic attraction, mechanical coupling, and centering.

17. The method of claim 15, where the overload circuit and one or more water seals in the wearable electronic device cooperate to maintain a water proofness to at least three atmospheres by needing a water seal for each of the arc-shaped, ferrous, metal contacts penetrating the surface of the wearable electronic device.

18. The method of claim 10, where the arc-shaped, ferrous, metal contacts take the form of two or more concentric metal contact rings on a surface of the wearable electronic device, which in combination with the magnets located in the external electrical charger are configured to magnetically to couple the charging pins in the external electrical charger, and where the male extension extending from the surface of the caseback coupling with the female receptor of the external electrical charger is configured to mechanically couple the external electrical charger to the wearable electronic device, where the mechanical coupling and the magnetic coupling creates an alignment in the three dimensions, the Z axis, the X axis, and the Y axis to allow a sufficient level of electrical current charge exchanged from the external electrical charger to the battery of the wearable electronic device to charge the battery from 0 to 100% to occur in less than sixty minutes while maintaining an external surface temperature around the concentric metal contact rings of no greater than 95 degrees Fahrenheit.

19. A wearable electronic device, comprising:
a housing;
a processor in the housing, wherein the processor is configured to process commands to present an onscreen display on a display screen to enable a user of the wearable electronic device to select a number of different operations;
a communication circuit in the housing, wherein the communication circuit is configured to transmit wirelessly to another computing device cooperating with the wearable electronic device;

a battery for the wearable electronic device;

a caseback for the wearable electronic device, where the caseback has multiple, arc-shaped, ferrous, metal contacts that serve a dual purpose of i) establishing a physical electrical input connection between a battery for the wearable electronic device and charging prongs of an external electrical charger and ii) establishing magnetic coupling between the wearable electronic device and multiple magnets in the external electrical charger to hold the metal contacts of the wearable electronic device and the charging prongs of the external electrical charger in place during a charging of the battery for the wearable electronic device; and a male extension extending from a surface of the caseback to couple into a female receptor of the external electrical charger, where the multiple, arc-shaped, ferrous, metal contacts' relationship with a positioning of the magnetics in the external electrical charger in combination with the male extension of the caseback coupling into the female receptor of the external electrical charger are magnetically and mechanically configured to establish and control an alignment of the metal contacts with the charging prongs/pins/contacts of the external electrical charger in three dimensions, a Z axis, an X axis, and a Y axis; and a non-transitory computer readable storage medium in the housing accessible to the processor and storing instructions executable by the processor to generate the number of different operations on the onscreen display.

20. The wearable electronic device of claim 19, where the male extension has an oval shape and a corresponding matching oval depression in the female receptor of the external electrical charger that allow a free rotation when mating the wearable electronic device and the external electrical charger before and during a charging of the battery process; and where an alignment of i) the multiple, arc-shaped, ferrous, metal contacts and the male extension of the wearable electronic device with ii) the magnets in the external electrical charger and the female receptacle of the external electrical charger establishes a flexible coupling between these devices that allows a 360 degree rotation axis for a physical and electrical coupling between the wearable electronic device and the external electrical charger, where the 360 degree rotation axis for the physical and electrical coupling is not limited to one or two positional relationships on how these devices couple together before and during the charging process for the battery.

* * * * *